United States Patent [19]
Warnow et al.

[11] 3,981,301
[45] Sept. 21, 1976

[54] PNEUMATICALLY CONTROLLED RESPIRATION DEVICE

[75] Inventors: Detlef Warnow; Hans-Jörg Ziebrecht, both of Lubeck, Germany

[73] Assignee: Dragerwerk Aktiengesellschaft, Germany

[22] Filed: June 26, 1975

[21] Appl. No.: 590,490

[30] Foreign Application Priority Data
June 27, 1974 Germany............................ 2430839

[52] U.S. Cl........................... 128/145.8; 137/624.14
[51] Int. Cl.².......................................... A61M 16/00
[58] Field of Search............ 128/145.8, 145.6, 145.5, 128/188; 137/624.14

[56] References Cited
UNITED STATES PATENTS

| | | | |
|---|---|---|---|
| 3,842,828 | 10/1974 | Bird | 128/145.8 |
| 3,889,669 | 6/1975 | Weigl | 128/145.8 |
| 3,903,881 | 9/1975 | Weigl | 128/145.6 |

*Primary Examiner*—Robert W. Michell
*Assistant Examiner*—Henry J. Recla
*Attorney, Agent, or Firm*—McGlew and Tuttle

[57] ABSTRACT

The device is of the type in which breathing gas, taken from a pressure-gas supply source through an injector and volumetrically metered in a pressure regulating valve, is supplied, in the inspiration phase, to the user and discharged, in the expiration phase, through an exhaling valve. A control space is divided, by an adjustable partition, into an inspiration chamber and an expiration chamber, and the ratio of the volumes of the two chambers is adjustable by adjustment of the partition. A frequency valve is connected to a source of control gas, and respective first pneumatic control elements connect the chambers, on their upstream sides, to the frequency valve and control supply of control gas to the chambers. Respective second pneumatic control elements connect the downstream sides of the chambers to a bistable storage which is connected to the exhaling valve. The first pneumatic control elements comprise NAND pneumatic elements, and the second pneumatic control elements comprise either identity gates or pairs of NAND elements connected in series with each other. The output sides of the bistable storage are connected to the respective first pneumatic control elements. When the inspiration chamber is filled with control gas, the bistable storage closes the exhaling valve and, when the expiration chamber is filled with control gas, the exhaling valve is opened.

10 Claims, 2 Drawing Figures

PNEUMATICALLY CONTROLLED RESPIRATION DEVICE

FIELD AND BACKGROUND OF THE INVENTION

The present invention relates to a pneumatically controlled respiration device in which the breathing gas, taken from a pressure-gas supply source through an injector and volumetrically metered in a pressure-regulating valve, is supplied, in the inspiration phase, to the user and discharged, in the expiration phase, through an exhaling valve.

A known pneumatically controlled respiration device comprises a combined pressure-regulating and control mechanism. This device includes a pressure chamber provided with an automatic inlet valve which, during the inspiration phase, admits pressure gas having a pressure corresponding to that in the lungs of the patient. In addition, the pressure chamber is provided with a controllable discharge mechanism. A final-control element is moved, during the inspiration phase, to close the inlet valve and, during the expiration phase, to open the same. The inhaling stroke is adjusted through an elastic tension member effective over the entire motion range of the final-control element, and through an additional elastic tension member which is effective only within the final step of this motion range.

The length of the expiration period is adjusted independently of the inspiration phase by means of the controllable discharge mechanism of the pressure chamber, by varying the cross-section of the discharge area.

The disadvantage of this device is the necessity of adjusting both the inspiration and the expiration time separately. This requires a great deal of skill, and a direct adjustment of the respiration frequency and of the respiration time ratio between the inspiration and expiration times is not possible (German Pat. No. 1,137,834).

In another known automatic respiration device, the flow of a breathing gas, supplied under the pressure of a gas source, is controlled by means of a control valve to which the breathing gas is delivered and which, in turn, is controlled by a controller switching in response to a certain inspiration volume and, thereby, closing the control valve, and reopening the same after a certain period of time of expiration. The controller is controlled, as a function of the passage of a certain gas volume, by a volume-control chamber mounted in parallel with a flow meter and releases a control impulse to close the control valve. The control valve is opened through a bellows as soon as the expiration phase is terminated and, up to this time, it is closed. The duration of the expiration phase may be varied by adjusting a discharge valve connected to the bellows.

This pneumatic device controls the inspiration phase in accordance with the inspiration volume and the expiration phase in time. The adjustment is complicated. Neither the respiration frequency nor the respiration time ratio can be adjusted directly (German Pat. No. 1,126,566).

Another known respiration device permits the release of the individual breathing phases, interfering in time with each other, both by the patient himself and by the device. The minimum time of the respective breathing phase, applied to the device as an input value or adjusted therein, causes a switching into the following breathing phase only upon expiration of the predetermined period of time, without a reversal effected by the spontaneous breathing of the patient. The automatic switching or release is effected by means of a relay circuit, and the reversal is effected through breathing by means of a control storage, in a well known manner.

In this device, the adjusted breathing phase is automatically switched over by electronic component parts requiring, aside from the necessary pressure-gas connection, a supply of electric energy. Electronic controls involve a complicated design and construction which, upon a failure, require a replacement of complete blocks (German Pat. No. 1,048,391).

It is common to all pneumatic systems that, for a controlled respiration, they do not permit a directly reproducible adjustment of the respiration frequency and the respiration time ratio. These values depend, inter alia, on the expiration phase. A certain experience is needed for an adjustment resulting in the desired frequency and the correct respiration time ratio with the right respiration volume.

SUMMARY OF THE INVENTION

The present invention is directed to an arrangement for controlling the respiration in pneumatically controlled respiration devices, making it possible, with a controllable amount of breathing gas, to adjust the respiration frequency and the respiration time ratio independently. The actuation of the device to this effect is ensured without a sensitive mechanism and while using only the pressure-gas supply.

In accordance with the invention, the inspiration and expiration chambers, forming a control space and adjustable in their volume relative to each other, are filled, each through a pneumatic control element mounted upstream, with control gas from a frequency valve and, to start the inhalation or exhalation phase, cause the exhaling valve, through pneumatic elements mounted downstream, to close or open, respectively. The pneumatic control elements mounted downstream of the inspiration and expiration chambers comprise a respective identity gate following each of the chambers and a bistable storage unit mounted thereafter.

The advantages obtained with the invention reside primarily in the fact that, aside from the adjustable respiration gas determining the amount of inspiration air in the time unit, both the respiration frequency and the respiration time ratio are made adjustable independently of each other. The respiration frequency is the reciprocal value of the total $T$ of the inspiration ($t_{In}$) and expiration ($t_{Ex}$) times $$(f = \frac{1}{T}).$$

Even with the variation of the respiration time ratio, i.e., the ratio of the inspiration time to the expiration time, the total time $T$ remains unchanged. Since $$f = \frac{1}{T} = \frac{1}{t_{In}+t_{Ex}},$$

a variation of the respiration time ratio does not result in a variation of the respiration frequency. The respiration frequency is changed by varying the control gas amount by means of the frequency valve, and the respiration time ratio is changed by varying the volumes of the inspiration and expiration chambers, whose volumes are adjustable relative to each other.

According to a development of the invention, the control space is divided, by a partition wall which is displaceable by means of an adjusting mechanism, into the inspiration and expiration chambers. Due to this useful design, a simple adjustment of the respiration time ratio is made possible without changing the respiration frequency, as already mentioned. Further, the advantages of a simple pneumatic control are fully utilized by the provision that the pneumatic control elements mounted upstream are NAND elements which are alternately triggered by the bistable storage unit and direct the control gas, dosed in the frequency valve, into the inspiration or expiration chamber, respectively, and that, by means of the pressure built up in the inspiration or expiration chamber and applied as switching pressure to the associated identity gate, the respective identity gate mounted downstream changes the state of the bistable storage unit. The inspiration phase is started in a simple manner so that, upon building up the switching pressure in the inspiration chamber for the identity gate, the bistable storage unit closes the exhaling valve.

Another very advantageous embodiment of the pneumatically controlled respiration device is obtained if the pneumatic control elements mounted downstream of the control space comprise two respective pairs of NAND elements mounted in series following each of the inspiration and expiration chambers, and a bistable storage unit mounted thereafter.

An object of the invention is to provide an improved pneumatically controlled respiration device.

Another object of the invention is to provide such an improved pneumatically controlled respiration device in which it is possible, with a controllable amount of breathing gas, to adjust the respiration frequency and the respiration time ratio independently of each other.

A further object of the invention is to provide such an improved pneumatically controlled respiration device in which these objectives are attained without a sensitive mechanism and using only the pressure-gas supply.

For an understanding of the principles of the invention, reference is made to the following description of typical embodiments thereof as illustrated in the accompanying drawings.

DESCRIPTION OF THE PREFERRED EMBODIMENTS

Figure 1:
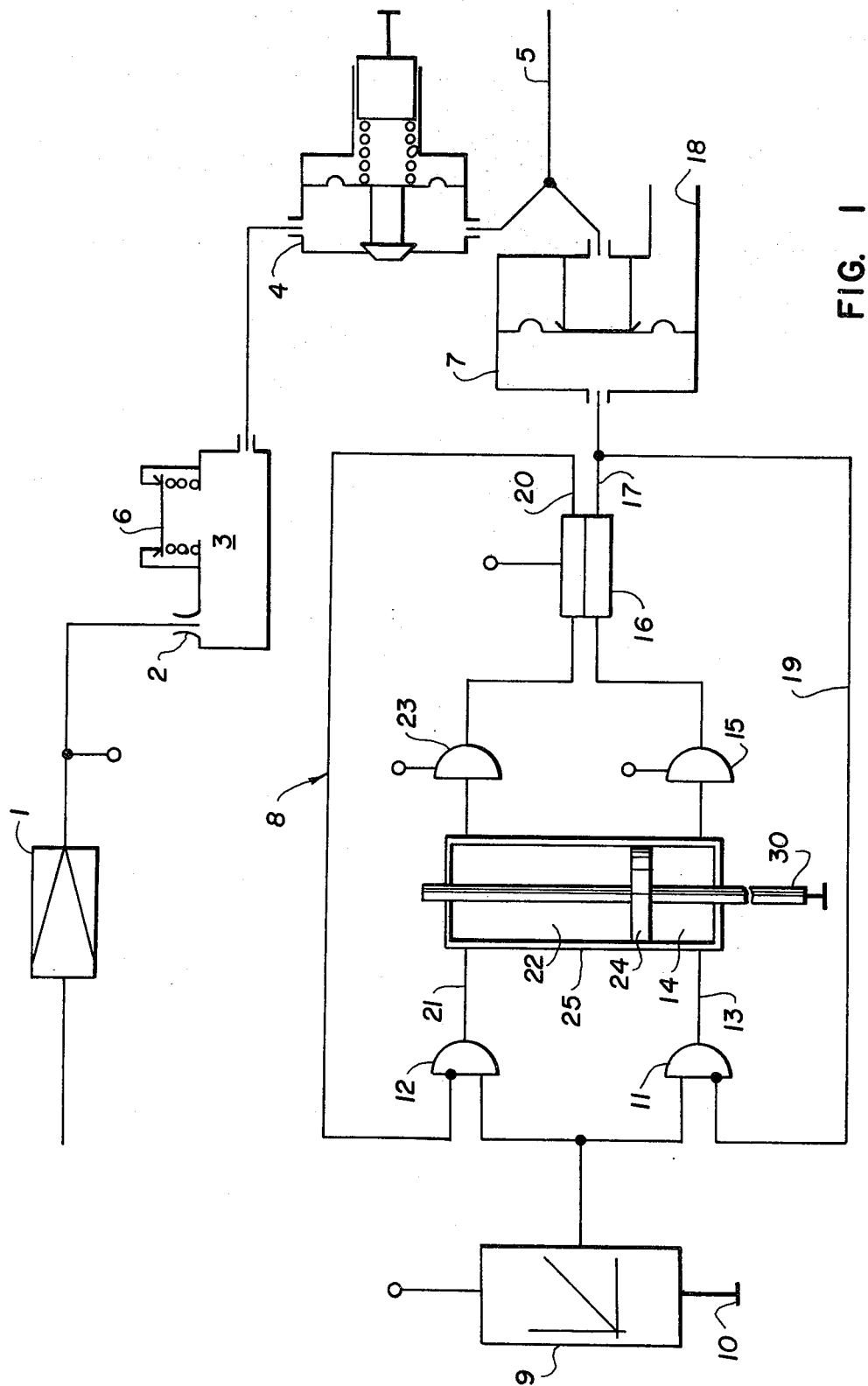
FIG. 1 is a diagrammatic illustration of one embodiment of an arrangement for controlling the respiration.

A pressure-reducing valve 1 reduces the inlet pressure to the working pressure $p$ necessary for operating the pneumatic elements. It also actuates an injector 2 directing the respiration gas into an element base 3 wherefrom the respiration gas passes, through a pressure-regulating valve 4 and a line 5, to the patient. Element base 3 comprises an additional-air valve 6 serving as an auxiliary air valve. Should the device fail in its operation, the patient can inspire air from the outside through valve 6. The patient expires or exhales through an exhaling valve 7 into the ambient atmosphere. Exhaling valve 7 determines the cycle of expiration and inspiration of the patient due to a corresponding triggering from a control device 8. A frequency valve 9, controlling the control gas, supplies control device 8 with a stream of control gas whose volume is adjustable by means of a hand wheel 10. The stream of control gas passes to NAND elements 11 and 12, of which always only one is enabled.

If NAND element 11 is enabled, the control gas coming from frequency valve 9 flows into an expiration chamber 14. Along with an inspiration chamber 22, expiration chamber 14 forms a fixed volume control space 25. A displaceable partition wall 24 is provided in control space 25, by which the volumes of the inspiration and expiration chambers are variable relative to each other. Partition wall 24 can be displaced by means of an adjusting mechanism 30.

An identity gate 15 is enabled as soon as the control gas has filled up expiration chamber 14 and the switching pressure for the identity gate is attained. Thereupon, identity gate 15 switches a bistable storage 16 to outlet 17, outlet 20 becomes pressureless, and exhaling valve 7 is triggered so that the respiration gas coming through pressure-regulating valve 4 cannot pass through opening 18 to the outside but flows through line 5 to the patient. Thus, the filling time of expiration chamber 14 determines the length of the expiration time $t_{ex}$.

At the same time, NAND element 11 is triggered through line 19, and line 13 becomes pressureless. The pressureless outlet of bistable storage 16 causes enabling of NAND element 12, whereupon the control gas coming from frequency valve 9 flows through line 21 into inspiration chamber 22. As soon as inspiration chamber 22 is filled with control gas and the switching pressure for an identity gate 23 is attained, identity gate 23 is enabled. Thereby, bistable storage 16 is switched to outlet 20 and outlet 17 becomes pressureless. Consequently, exhaling valve 7 opens and the respiration gas coming from pressure-regulating valve 4 can flow to the outside through outlet 18. The patient can exhale.

Thus, the filling time of inspiration chamber 22 determines the length of the inspiration time $t_{In}$. The sum of times $t_{Tn} + t_{Ex}$ is equal to T. If now the partition wall 24 of control space 25 is displaced by means of adjusting mechanism 30, only the partial times $t_{In}$ and $t_{Ex}$ are changed, not the total time T. Since the reciprocal value of T is equal to the respiration frequency $f$, a variation of the ratio of the respiration times $t_{In}:t_{Ex}$ does not change anything in the respiration frequency. The respiration frequency can be changed only by changing the volume of the control gas, by means of the hand wheel 10 of frequency valve 9. Thereby, a greater amount of gas causes a faster filling of inspiration 22 or expiration chamber 14 and, in consequence, a shorter time T. In accordance with the relation $$f = \frac{1}{T},$$

a shorter time T means a higher respiration frequency $f$. Since a changed total volume of control gas does not change the ratio of the filling times of chambers 14 and 22, i.e., does not change the relation of $t_{In}:t_{Ex}$, with a variation of the respiration frequency, the respiration time ratio remains constant.

Figure 2:
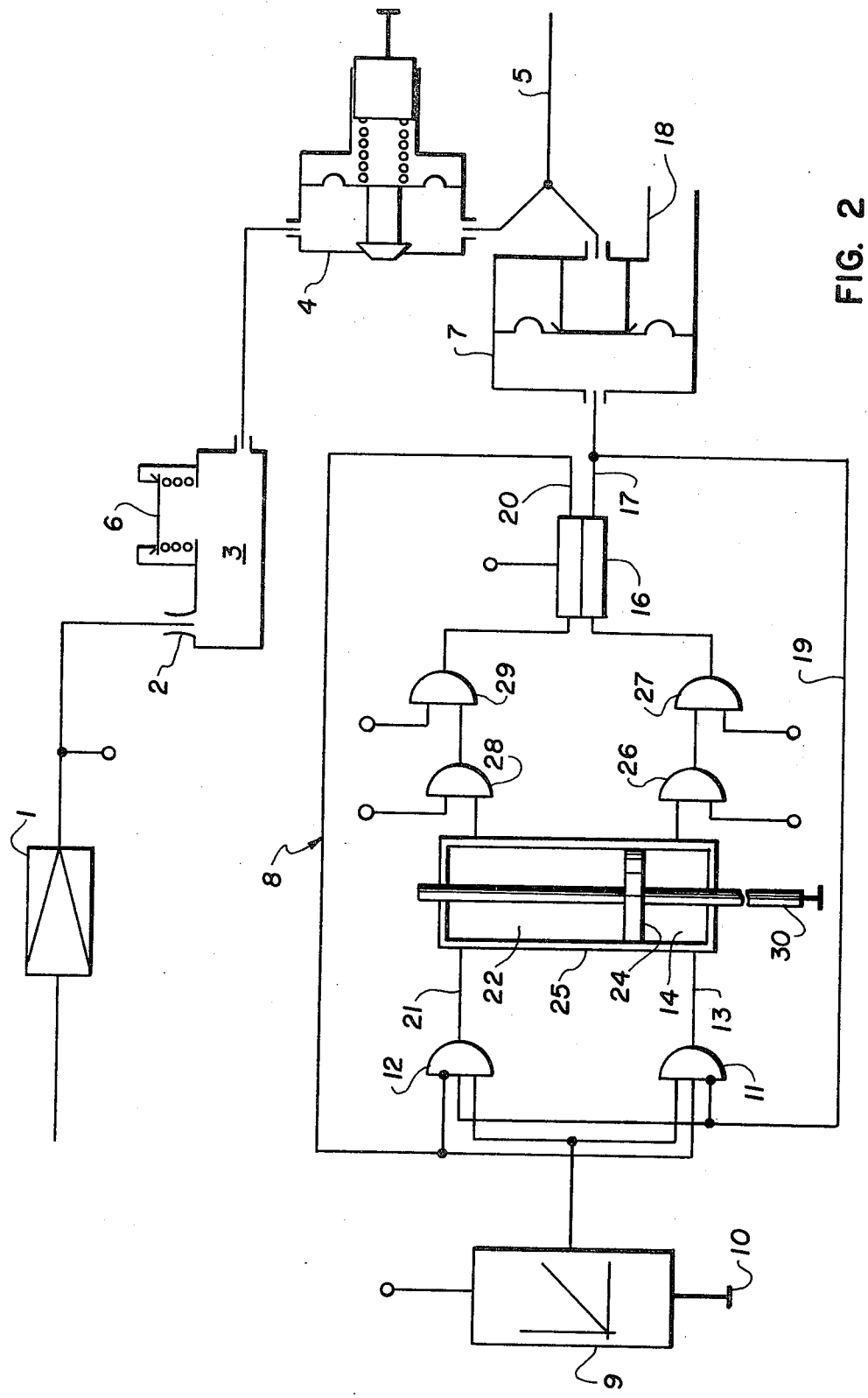
FIG. 2 is a view similar to FIG. 1 illustrating another embodiment of the same arrangement.

In the embodiment of FIG. 2, between control space 25 and bistable storage 16, downstream of both inspiration chamber 22 and expiration chamber 14, two series connected NAND elements 26 and 27 as well as 28 and 29 are provided in each of the paths. As to their basic operation, the two arrangements for controlling the respiration shown in FIGS. 1 and 2 do not differ from each other. However, the arrangement with two series connected NAND elements according to FIG. 2 needs a smaller opening power at the switching of the respiration phases.

While specific embodiments of the invention have been shown and described in detail to illustrate the application of the principles of the invention, it will be understood that the invention may be embodied otherwise without departing from such principles.

What is claimed is:

1. In a pneumatically controlled respiration device in which breathing gas, taken from a pressure-gas supply source through an injector and volumetrically metered in a pressure regulating valve, is supplied, in the inspiration phase, to the user and discharged, in the expiration phase, through an exhaling valve, the improvement comprising, in combination, a source of respiration gas; a respiration gas enclosure element; an injector connected between said source and said enclosure element for delivering respiration gas thereto; a pressure regulating valve connected to said enclosure element; an exhaling valve means having an opening to atmosphere; a user line connected to said pressure regulating valve and to said opening of said exhaling valve means; said pressure regulating valve including means for volumetrically metering the respiration gas delivered to said user line; said exhaling valve means normally establishing communication between said user line and said opening for the expiration phase and, responsive to application of a control pressure thereto, blocking communication between said user line and said opening to initiate the inspiration phase; means forming a fixed volume control space divided into an inspiration chamber and an expiration chamber; means operable to adjust the ratio of the volumes of said chambers; a source of control gas under pressure; a frequency valve connected to said source of control gas, first and second pneumatic control elements; said first and second elements directly connecting said inspiration and expiration chambers, respectively, on the upstream sides, to said frequency valve and each including means operable, only when enabled, to supply control gas to the associated chamber from said frequency valve for filling of the associated chamber with control gas; said first and second pneumatic control element includes means for enabling the same only when control gas is supplied thereto solely from said frequency valve; third and fourth pneumatic elements each having inputs connected, respectively, to said source of control gas and directly to the downstream sides of said inspiration and expiration chambers, respectively, and each having an output; each of said third and fourth pneumatic elements including means responsive to filling of the associated chamber with control gas for connecting the source of control gas to its output; the output of each second pneumatic element being without pressure until the associated chamber has been filled with control gas; means connecting the output of each third and fourth pneumatic elements to each of said first and second pneumatic control elements, respectively, whereby said first and second pneumatic control elements are responsive to filling of the associated chamber with control gas and thereby, the output of said third and fourth pneumatic elements such that each first and second pneumatic control element is no longer enabled and blocks flow of control gas from said frequency valve to each associated chamber so that the control gas in the associated chamber is discharged through the associated third and fourth pneumatic element; and means connecting the output of the respective fourth pneumatic element connected to said expiration chamber to said exhaling valve means for applying control pressure to said exhaling valve means for closing said opening to atmosphere to initiate the inspiration phase; the respective first pneumatic control element connected to said inspiration chamber being enabled, due to the lack of pressure at the output of the respective third pneumatic element connected to said inspiration chamber, to initiate filling of said inspiration chamber with control gas from said frequency valve; whereby the lengths of the respective phases of the respiration cycle are determined solely by the filling times, and thus the volumes, of the respective chambers.

2. In a pneumatically controlled respiration device, the improvement claimed in claim 1, including a partition wall dividing said control space into said inspiration and expiration chambers; and means operable to adjust said partition wall to adjust the ratio of the volumes of said inspiration and expiration chambers.

3. In a pneumatically controlled respiration device, the improvement claimed in claim 2, including an adjusting mechanism connected to said partition, and operable to adjust the same.

4. In a pneumatically controlled respiration device, the improvement claimed in claim 1, in which said pneumatic elements connecting the downstream side of said chambers to said exhaling valve means comprise respective identity gates connected to the downstream side of each chamber; and a bistable storage unit connected to the outputs of both identity gates and to said exhaling valve means.

5. In a pneumatically controlled respiration device, the improvement claimed in claim 2, in which said first and second pneumatic control elements comprise pneumatic NAND elements triggered alternately by said bistable storage unit to direct the control gas from said frequency valve into the associated chambers.

6. In a pneumatically controlled respiration device, the improvement claimed in claim 4, in which the pressure built up in each chamber is supplied as a switching pressure to the associated identity gate connected on the downstream side thereof; the associated identity gate, when having the pressure applied thereto, changing the state of said bistable storage unit.

7. In a pneumatically controlled respiration device, the improvement claimed in claim 6 in which said first and second pneumatic control elements comprise pneumatic NAND elements alternately triggered by said bistable storage unit.

8. In a pneumatically controlled respiration device, the improvement claimed in claim 4, in which, responsive to build up of switching pressure in said inspiration chamber and acting upon the associated identity gate connected to the downstream side thereof, said bistable storage unit closes said opening of said exhaling valve means.

9. In a pneumatically controlled respiration device, the improvement claimed in claim 8, in which, responsive to operation of said bistable storage unit to close said opening of said exhaling valve means, the respective second pneumatic control elements connected to the upstream side of said inspiration chamber is triggered to release pressure from said inspiration chamber and the respective second pneumatic control element connected to the upstream side of said expiration chamber is triggered to connect said expiration chamber to said frequency valve to effect switching of said bistable storage to a state effecting opening of said opening of said exhaling valve means.

10. In a pneumatically controlled respiration device, the improvement claimed in claim 1, in which said third and fourth pneumatic elements connecting the downstream side of said chamber to said exhaling valve means each comprise respective pairs of series-connected pneumatic NAND elements connected to the downstream sides of said chambers; and a bistable storage unit connected to both pairs of pneumatic NAND elements and to said exhaling valve means.

* * * * *